United States Patent
Seino et al.

(10) Patent No.: US 6,492,167 B2
(45) Date of Patent: *Dec. 10, 2002

(54) UBIQUITOUS POTASSIUM-CHANNEL PROTEINS AND THEIR GENES

(75) Inventors: Susumu Seino, Inohana Shukusha of Chiba University 1-103, Inohana 1-8-1, Chuo-ku (JP); Nobuya Inagaki, Chiba (JP)

(73) Assignees: Susumu Seino, Chiba (JP); JCR Pharmaceuticals Co., Ltd., Hyogo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/166,963

(22) Filed: Oct. 6, 1998

(65) Prior Publication Data

US 2002/0068824 A1 Jun. 6, 2002

Related U.S. Application Data

(63) Continuation of application No. 08/614,155, filed on Mar. 12, 1996, now Pat. No. 5,919,692.

(30) Foreign Application Priority Data

Sep. 18, 1995 (JP) .............................. 7-264942

(51) Int. Cl.[7] .............................. C12N 1/15; C12N 1/21; C12N 5/10; C12N 15/12; C12N 15/63
(52) U.S. Cl. ............... 435/325; 435/252.3; 435/254.11; 435/320.1; 536/23.1; 536/23.5; 536/24.3; 536/24.31
(58) Field of Search ................... 536/23.1, 23.5, 536/24.3, 24.31; 435/320.1, 325, 252.3, 254.11

(56) References Cited

FOREIGN PATENT DOCUMENTS

| WO | 94/19464 | 9/1994 |
|---|---|---|
| WO | 95/04820 | 2/1995 |

OTHER PUBLICATIONS

Bowie et al., Science 247:1306–1310, 1990.*
Wells, Biochemistry 29:8509–8517, 1990.*
Ngo et al., The Protein Folding Problem and Teritary Structure Predicition, Merz et al., eds., Birkhauser, Boston, pp. 492–495, 1994.*
Schulz et al., Principles of Protein Structure, Springer–Verlag, New York, pp. 14–16, 1979.*
Asford et al. Nature 370:456–459, Aug. 1994.*
J. Biol Chem, Mar. 17, 1995, 270 (11) P5691–4, United States, XP002019860, Susumu Seino Inohana Shukusha Chiba University: "Cloning and functional characterzation of a novel ATP–sensitive potassium channel ubiquitously expressed in rat tissues, including pancreatic islets, pituitary, skeletal muscle, and heart".
Genomics, Nov. 1, 1995, 30 (1) P102–4, United States, XP000612109 Inagaki N et al: "cDNA sequence, gene structure, and chromosomal localization of the human ATP–sensitive potassium channel, uKATP–1, gene (KCNJ8)".

\* cited by examiner

*Primary Examiner*—Elizabeth Kemmerer
(74) *Attorney, Agent, or Firm*—Jacobson Holman PLLC

(57) ABSTRACT

The present invention provides novel ATP-sensitive potassium-channel proteins which are present ubiquitously in the living bodies of animals, and their genes.

5 Claims, 5 Drawing Sheets

FIG. 1

```
        10          20          30          40          50          60
MLARKSIIPE  EYVLARIAAE  NLRKPRIRDR  LPKARFIAKS  GACNLAHKNI  REQGRFLQDI 70          80          90         100         110         120
FTTLVDLKWR  HTLVIFTMSF  LCSWLLFAIM  WWLVAFAHGD  IYAYMEKSGM  EKSGLESTVC 130         140         150         160         170         180
VTNVRSFTSA  FLFSIEVQVT  IGFGGRMMTE  ECPLAITVLI  LQNIVGLIIN  AVMLGCIFMK 190         200         210         220         230         240
TAQAHRRAET  LIFSRHAVIA  VRNGKLCFMF  RVGDLRKSMI  ISASVRIQVV  KKTTTPEGEV 250         260         270         280         290         300
VPIHQLDIPV  DNPIESNNIF  LVAPLIICHV  IDKRSPLYDI  SATDLANQDL  EVIVILEGVV 310         320         330         340         350         360
ETTGITTQAR  TSYIAEEIQW  GHRFVSIVTE  EEGVYSVDYS  KFGNTVKVAA  PRCSARELDE 370         380         390         400         410         420
KPSILIQTLQ  KSELSHQNSL  RKRNSMRRNN  SMRRNNSIRR  NNSSLMVPKV  QFMTPEGNQN 430         440         450         460         470         480
TSES*.........  .................  .................  .................  .................  .................
```

FIG. 3

```
        10          20          30          40          50          60
MLARKSIIPE  EYVLARIAAE  NLRKPRIRDR  LPKARFIAKS  GACNLAHKNI  REQGRFLQDI 70          80          90         100         110         120
FTTLVDLKWR  HTLVIFTMSF  LCSWLLFAIM  WWLVAFAHGD  IYAYMEKGIT  EKSGLESAVC 130         140         150         160         170         180
VTNVRSFTSA  FLFSIEVQVT  IGFGGRMMTE  ECPLAITVLI  LQNIVGLIIN  AVMLGCIFMK 190         200         210         220         230         240
TAQAHRRAET  LIFSRHAVIA  VRNGKLCFMF  RVGDLRKSMI  ISASVRIQVV  KKTTTPEGEV 250         260         270         280         290         300
VPIHQQDIPV  DNPIESNNIF  LVAPLIICHV  IDKRSPLYDI  SATDLVNQDL  EVIVILEGVV 310         320         330         340         350         360
ETTGITTQAR  TSYIAEEIQW  GHRFVSIVTE  EEGVYSVDYS  KFGNTVRVAA  PRCSARELDE 370         380         390         400         410         420
KPSILIQTLQ  KSELSHQNSL  RKRNSMRRNN  SMRRSNSIRR  NNSSLMVPKV  QFMTPEGNQC 430         440         450         460         470         480
PSES*.........  .................  .................  .................  .................  .................
```

FIG. 2

```
         10         20         30         40         50         60
    ATGTTGGCCA GAAAGAGTAT CATCCCGGAG GAGTATGTGC TGGCGCGCAT CGCCCGCAGAG
         70         80         90        100        110        120
    AACCTGCGCA AGCCGCGCAT CCGAGACCGC CTCCCCAAAG CCCGCTTCAT CGCCAAGAGC
        130        140        150        160        170        180
    GGGGCCTGCA ACCTGGCGCA TAAGAACATC CGTGAGCAAG GACGCTTTCT ACAGGACATC
        190        200        210        220        230        240
    TTCACCACCT TGGTGGACCT GAAATGGCGC CACACGCTGG TCATCTTTAC CATGTCCTTC
        250        260        270        280        290        300
    CTCTGCAGCT GGCTGCTCTT CGCTATCATG TGGTGGCTGG TGGCCTTTGC CCATGGGGAC
        310        320        330        340        350        360
    ATCTATGCTT ACATGGAGAA AAGTGGAATG GAGAAAAGTG GTTTGGAGTC CACTGTGTGT
        370        380        390        400        410        420
    GTGACTAATG TCAGGTCTTT CACTTCTGCT TTTCTCTTCT CCATTGAAGT TCAAGTTACC
        430        440        450        460        470        480
    ATTGGGTTTG GAGGGAGGAT GATGACAGAG GAATGCCCTT TGGCCATCAC GGTTTTGATT
        490        500        510        520        530        540
    CTCCAGAATA TTGTGGGTTT GATCATCAAT GCAGTCATGT TAGGCTGCAT TTTCATGAAA
        550        560        570        580        590        600
    ACAGCTCAGG CTCACAGAAG GGCAGAAACT TTGATTTTCA GCCGCCATGC TGTGATTGCC
        610        620        630        640        650        660
    GTCCGAAATG GCAAGCTGTG CTTCATGTTC CGAGTGGGTG ACCTGAGGAA AAGCATGATC
        670        680        690        700        710        720
    ATTAGTGCCT CTGTGCGCAT CCAGGTGGTC AAGAAAACAA CTACACCTGA AGGGGAGGTG
        730        740        750        760        770        780
    GTTCCTATTC ACCAACTGGA CATTCCTGTT GATAACCCAA TCGAGAGCAA TAACATTTTT
        790        800        810        820        830        840
    CTGGTGGCCC CTTTGATCAT CTGCCACGTG ATTGACAAGC GCAGTCCCCT GTATGACATC
        850        860        870        880        890        900
    TCAGCAACTG ACCTGGCCAA CCAAGACTTG GAGGTCATAG TTATTCTGGA AGGAGTGGTT
        910        920        930        940        950        960
    GAAACTACTG GCATCACCAC ACAAGCACGA ACCTCCTACA TTGCTGAGGA GATCCAATGG
        970        980        990       1000       1010       1020
    GGCCACCGCT TTGTGTCCAT TGTGACTGAG GAAGAAGGAG TGTATTCTGT GGATTACTCC
       1030       1040       1050       1060       1070       1080
    AAATTTGGCA ACACTGTTAA AGTAGCTGCT CCACGGTGCA GTGCCCGAGA GCTGGATGAG
       1090       1100       1110       1120       1130       1140
    AAACCTTCCA TCCTTATTCA GACCCTCCAA AAGAGTGAAC TGTCTCATCA AAATTCTCTG
       1150       1160       1170       1180       1190       1200
    AGGAAGCGCA ACTCCATGAG AAGAAACAAT TCCATGAGGA GGAACAATTC TATCCGAAGG
       1210       1220       1230       1240       1250       1260
    AACAATTCTT CCCTCATGGT ACCAAAGGTG CAATTTATGA CTCCAGAAGG AAATCAAAAC
       1270       1280       1290       1300       1310       1320
    ACATCGGAAT CATGA
```

FIG. 4

```
         10         20         30         40         50         60
ATGCTGGCCA GGAAGAGCAT CATCCCGGAG GAGTATGTGC TGGCCCGCAT CGCGGCGGAG
         70         80         90        100        110        120
AACCTGCGCA AACCGCGCAT CCGCGACCGC CTCCCCAAAG CCCGCTTCAT CGCCAAGAGC
        130        140        150        160        170        180
GGAGCCTGCA ACCTGGCTCA CAAGAACATC CGAGAGCAAG GTCGCTTCCT GCAGGACATC
        190        200        210        220        230        240
TTCACCACCT TGGTAGACCT GAAGTGGCGT CACACGCTGG TCATCTTCAC CATGTCCTTC
        250        260        270        280        290        300
CTCTGCAGCT GGCTGCTCTT CGCTATCATG TGGTGGCTGG TGGCCTTCGC CCACGGGGAC
        310        320        330        340        350        360
ATCTATGCTT ACATGGAGAA AGGCATCACG GAGAAGAGTG GCCTGGAGTC TGCCGTCTGT
        370        380        390        400        410        420
GTGACCAATG TCAGGTCATT CACTTCTGCG TTTCTCTTCT CCATCGAGGT TCAAGTGACC
        430        440        450        460        470        480
ATTGGGTTTG GAGGGAGAAT GATGACTGAG GAGTGCCCTC TGGCCATCAC GGTTTTGATT
        490        500        510        520        530        540
CTGCAGAACA TTGTGGGTCT GATCATCAAC GCGGTCATGT TGGGCTGCAT CTTCATGAAG
        550        560        570        580        590        600
ACGGCCCAGG CCCACAGAAG GGCAGAGACG CTGATTTTCA GCCGCCATGC TGTAATTGCG
        610        620        630        640        650        660
GTCCGTAATG GCAAGCTGTG CTTCATGTTC CGGGTGGGTG ACCTGAGGAA AAGCATGATC
        670        680        690        700        710        720
ATTAGCGCCT CGGTGCGCAT CCAGGTGGTC AAGAAAACCA CGACGCCAGA AGGAGAGGTG
        730        740        750        760        770        780
GTGCCTATTC ACCAGCAGGA CATCCCTGTG GATAATCCCA TCGAGAGCAA TAACATCTTC
        790        800        810        820        830        840
CTAGTGGCCC CTTTGATCAT CTGCCATGTG ATTGATAAGC GTAGCCCCCT GTACGATATC
        850        860        870        880        890        900
TCAGCCACTG ACCTTGTCAA CCAAGACCTG GAGGTCATAG TGATTCTCGA GGGCGTGGTG
        910        920        930        940        950        960
GAAACCACGG GCATCACCAC GCAAGCGCGG ACCTCCTACA TTGCAGAGGA GATCCAGTGG
        970        980        990       1000       1010       1020
GGACACCGCT TCGTGTCGAT TGTGACTGAG GAGGAGGGAG TGTACTCTGT GGACTATTCT
       1030       1040       1050       1060       1070       1080
AAATTTGGTA ATACTGTGAG AGTGGCGGCG CCAAGATGCA GTGCCCGGGA GCTGGACGAG
       1090       1100       1110       1120       1130       1140
AAACCTTCCA TCTTGATTCA GACCCTCCAA AAGAGTGAAC TGTCGCACCA GAATTCTCTG
       1150       1160       1170       1180       1190       1200
AGGAAGCGCA ACTCTATGAG AAGAAACAAC TCCATGAGGA GGAGCAACTC CATCCGGAGG
       1210       1220       1230       1240       1250       1260
AATAACTCTT CCCTCATGGT GCCCAAGGTG CAATTCATGA CTCCAGAAGG AAACCAGTGC
       1270       1280       1290       1300       1310       1320
CCATCAGAAT CATGA......
```

UBIQUITOUS POTASSIUM-CHANNEL PROTEINS AND THEIR GENES

This is a continuation of application Ser. No. 08/614,155 filed Mar. 12, 1996 now U.S. Pat. No. 5,919,692.

The present invention relates to proteins for novel ATP-sensitive potassium channels, $huK_{ATP}$-1 and $ruK_{ATP}$-1, that are expressed in various tissues of human and rat origins, and to genes encoding the same. The said proteins and genes can be used as diagnostic and therapeutic agents for potassium-channel related diseases such as diabetes, hypertension and endocrine insufficiencies.

BACKGROUND OF THE INVENTION

The etiology for diabetes is known to be mostly owing to disturbances of insulin secretion in the pancreatic β-cells. Consequently, elucidation of the molecular mechanism of insulin secretion is expected to play an important role in the clarification of causes for diabetes and the development of therapeutic agents against diabetes, but no detail has yet been made known on such molecular mechanism.

It has already been made clear that the ATP-sensitive potassium channel ($K_{ATP}$) being present on the cellular membrane plays a leading role in the cellular functions such as secretions and muscular contraction by coupling the state of metabolism in the cells with the membrane potential.

The $K_{ATP}$ channel was first discovered in the cardiac muscle in 1983 [Noma, A., Nature 305:147 (1983)] and was thereafter confirmed to be present in tissues such as the pancreatic β-cell [Cook, D. L. et al., Nature 311: 271 (1984), Misler, S. et al., Proc. Natl. Acad. Sci. U.S.A. 83: 7119 (1986)], pituitary [Bernardi, H. et al., Proc. Natl. Acad. Sci. U.S.A., 90:1340 (1993)]. skeletal muscle [Spruce, A. E., et al., Nature, 316: 736 (1985)] and brain.

In addition, it has been suggested that there exists the molecular heterogeneity of such $K_{ATP}$ channels [Ashcroft, F. M., Annu. Rev. Neurosci. 11: 97 (1988)].

Particularly in the pancreatic β-cells, ATP produced by the metabolism of glucose brings about calcium ion inflow from the calcium channel by closing the $K_{ATP}$ channel to cause depolarization, resulting in secretion of insulin. As is evident from this, the $K_{ATP}$ channel plays a leading role in regulating the secretion of insulin.

The $K_{ATP}$ channel belongs to a potassium channel family exhibiting electrophysiologically inward rectification, whereby the potassium channel family exhibiting inward rectification is classified into the four subfamilies, ROMK1, IRK1, GIRK1 and $cK_{ATP}$-1, on the basis of the degree of amino acid sequence identity.

Nevertheless, there has not been clarified the molecular architecture for the $K_{ATP}$ channel in the pancreatic β-cells. In addition, no information has been disclosed on the novel ATP-sensitive potassium channels ($huK_{ATP}$-1 and $ruK_{ATP}$-1) of the present invention for the detailed protein structure and the formation of complexes with other proteins, for example, the sulfonylurea binding protein.

SUMMARY OF THE INVENTION

In order to achieve the isolation, identification and functional analyses of a novel membrane channel, there are required the sophisticated techniques, such as molecular biological technique, cellular biological technique and electro-physiological technique.

Such being the case, the present inventors made ample and full use of such techniques to isolate human and rat genomes and cDNAs encoding the novel $K_{ATP}$ channel ($uK_{ATP}$-1) expressed in different tissues of mammalians and to identify their amino acid sequences (see FIGS. 1, 2, 3 and 4). The identified $uK_{ATP}$-1 channel was expressed in the Xenopus oocyte system and mammalian cell lines.

Electrophysiological analysis demonstrated that $uK_{ATP}$-1 is an ATP-sensitive potassium channel exhibiting inward rectification. The $uK_{ATP}$-1 channel being expressed ubiquitously in tissues of mammalians inclusive of man and rats is involved in the maintenance of the membrane potential through the basal energy metabolism.

As is described in the above, the present invention relates to an ATP-sensitive potassium channel ($uK_{ATP}$-1) which is ubiquitously present in mammalians, and encompasses the ATP-sensitive potassium channel proteins, identified DNA sequences encoding the same, plasmid having such sequences incorporated therein and furthermore recombinant cells (tranformants) having such plasmid transfected therein. In addition, this invention comprises the isolated $UK_{ATP}$-1 proteins and recombinant proteins, their related materials such as agonists and antagonists, and drug designs inclusive of diagnostics and drugs for gene therapy.

DETAILED DESCRIPTION $huK_{ATP}$-1 of a human origin is composed of 424 amino acid residue (See FIG. 1 (SEQ ID NO: 1)) with a molecular weight of 47,965, while the one of a rat origin is likewise composed of 424 amino acid residue (see FIG. 4 (SEQ ID NO: 4)) with a molecular weight of 47,960. These two potassium channels exhibit 98% amino acid sequence identity, and such a marked homology leads us to the assumption that $uK_{ATP}$-1 performs common, structurally and functionally basic actions in all mammalian cells. Among others, $uK_{ATP}$-1 participates in the membrane potential and energy metabolism, suggesting that it could find application as a drug substance acting to prevent disturbances under unusual, extreme metabolic conditions inclusive of endocrine diseases, e.g. diabetes, starvation and ischemia.

For example, the inflow and outflow of calcium ions caused by the opening and closing of $UK_{ATP}$-1 during the onset of ischemia is closely connected with ischemic disturbances. In other words, there is a possibility that the agonists and antagonists for the opening and closing of $uK_{ATP}$-1 would constitute a suppressory agent against ischemic disturbances.

From the comparative studies of $huK_{ATP}$-1 and $ruK_{ATP}$-1 with other potassium channels for the amino acid sequence, it was confirmed that $uK_{ATP}$-1 of the present invention belongs to a novel family of the inward rectifier potassium channels; the central region of the $uK_{ATP}$-1 protein showed incresed homology with other inward rectifier potassium channels. A hydropathy plot indicated the presence of two hydrophobic regions, which are composed of two transmembrane regions characteristic of the inward rectifier potassium channels and one pore region [Nicholas, C. G., Trends Pharmacol. Sci., 14: 320 (1993), Jan, L. Y. and Jan, Y. N., Nature, 371: 119 (1994)].

With reference to $ruK_{ATP}$-1 (Inagaki, N. et al., J. B. C., 270: 5691 (1995)], it was reported that in the second intracellular region, there are two potential cAMP-dependent protein kinase phosphorylation sites (Thr-234 and Ser-385) and seven potential protein kinase C dependent phosphorylation sites (Ser-224, Thr-345, Ser-354, Ser-379, Ser-385, Ser-391 and Ser-397), while there are one (Thr-63) and four potential casein kinase II dependent phosphorylation sites (Thr-234, Ser-281, Thr-329 and Ser-354) in the first and second intracellular regions, respectively, with no N-linked glycosylation site being present in the intracellular regions. The same findings were obtained with $huK_{ATP}$-1 [Inagaki, N., et al., in press (1995)].

Then, the present inventors identified the nucleotide sequences and entire amino acid sequences of $huK_{ATP}$-1 and $ruK_{ATP}$-1, thus enabling not only proteins themselves of $huK_{ATP}$-1 and $ruK_{ATP}$-1 but also their mutants to be synthesized in large quantities by expressing the DNAs encoding $huK_{ATP}$-1 and $ruK_{ATP}$-1 and their mutants in bacteria or animal cells with use of the known genetic engineering techniques. It is furthermore added that $huK_{ATP}$-1 and its fragments are useful for the hybridization diagnosis of depleted $huK_{ATP}$-1 DNA, with the mutants of $huK_{ATP}$-1 being of use in the studies on the sugar metabolism in cells, particularly insulin-dependent and independent diabetes.

The DNAs of novel $huK_{ATP}$-1 and $ruK_{ATP}$-1 according to the present invention were identified based on a cDNA library and genome library. The DNA encoding $huK_{ATP}$-1 shows a length of about 9.7 kb, being composed of three exons and is present on the chromosome at 12p11.23. The chromosomal DNA can be obtained by probing a genome DNA library with use of cDNAs for $uK_{ATP}$-1 and its fragment, as well. The isolated $uK_{ATP}$-1 DNA can easily be subjected to nucleotide depletion, insertion or replacement by the known techniques to prepare its mutants.

By employing the known techniques, it is easy to link nucleotide sequences encoding other proteins or synthetic polypeptides to $uK_{ATP}$-1 or its variants at the 5' and 3' ends to thereby prepare fusion proteins, or derivatives thereof.

For example, a fusion protein is prepared as a precursor protein and undergoes cleavage in vivo or in vitro to thereby perform functions; such fusion protein provides target-tissue and membrane orientation in addition to its proper function. In such a case, the fusion proteins contain sugar-chain binding amino acids, and can be modified to derivatives having tissue orientation or physiological activities activated by adding new sugar chains.

In order to produce $uK_{ATP}$-1, its mutants or their derivatives, the corresponding coding DNA is incorporated into a reproducible plasmid, and host cells being transformed with such plasmid are incubated. The host cells include bacteria, yeasts and animal cells.

Prokaryotes such as bacteria are suited for the cloning of deoxyribonucleotides. For example, pER 322 plasmid derived from *E. coli* contains a gene resistant to ampicillin or tetracycline and can provide a practical means of identifying the transformed cells. Furthermore, the microbial plasmids contain a promoter which can be used to express their proteins themselves. In addition to prokaryotes, eukaryotes such as yeasts can work well, with a plasmid YRp7 being utilizable especially in allowing the expression in yeasts of the species Saccharomyces [Stinchomb et al., Nature, 282: 39 (1979)].

Animal cells are also used as a host, and particularly the incubation of vertebra cells is employable easily and constitutes a conventional means [Krause and Paterson, Tissue Culture, Academic Press (1973)]. As the cell lines, there are mentioned AtT-20, Hela cells, Chinese hamster ovary (CHO), COSM6, COS-7 and the like. The promoters of Polyomavirus, Adenovirus 2, Cytomegalovirus and Simian virus 40 are used to control the function of expression plasmid in such cell lines, wherein pCMV is a plasmid which finds widened application in the expression systems of animal cells [Thomsen et al., PNAS, 81: 659 (1984)].

The DNA sequences for the channel protein and $huK_{ATP}$-1 and $ruK_{ATP}$-1 according to the present invention begin with the initiation codon "ATG". In cases where the recombinant cells are used to synthesize such protein, there is no need to add ATG to the desired DNA, thus making the manipulation easy. When $uK_{ATP}$-1 is expressed in a prokaryote transformed with *E. coli*, consequently, there is generally synthesized a protein of the amino acid sequence beginning with Met. The N-terminated met of the resultant protein may be eliminated according to the purpose of application.

In cases in which $uK_{ATP}$-1 is synthesized in recombinant animal cells, similarly, proteins having Met contained or eliminated at the N-terminal are bio-synthesized, and both are useful for individually intended application purposes.

$uK_{ATP}$-1 and its fragments can be administered to animals for their immunization to thereby produce antibodies. Also, immunization of animals permits a monoclonal antibody to be produced from cells secreting the desired antibody.

It has become easy to prepare $uK_{ATP}$-1 in large quantities, thus providing better understanding of the same at the molecular level. Accordingly, the production of $uK_{ATP}$-1 and its mutants or analogs raises the possibility to develop diagnostics or therapeutics for the channel-protein related diseases.

In particular, such proteins can be utilized in the procedures of investigating into a substance suited for diagnostics and therapeutics, or a substance that exerts agonistic or antagonistic action on $uK_{ATP}$-1. For example, a testing procedure with animal cells can be conducted by injecting cRNA for $uK_{ATP}$-1 into cells to conduct expression, followed by addition of sulfonylurea to study their interactions [Kayano, T. et al., J. Biol. Chem., 265: 13276 (1990), Example 4].

Additionally, the pertinent information has been obtained on the DNA sequence of $uK_{ATP}$-1, facilitating DNA or RNA encoding their fractional sequences to be prepared. Such relatively short DNA sequences possess the capability to hybridize with the gene to be selected, and can find application as a probe, which probe is effective for detection of cDNAs in different tissues.

The probe as prepared with use of $uK_{ATP}$-1 can be utilized to produce nucleic acids capable of hybridization from a variety of organisms and their tissues. The resultant nucleic acids may be the same type as $uK_{ATP}$-1 or its isoform and include nucleic acids encoding the novel proteins.

The prepared probe is utilizable in the gene diagnosis of potassium-channel related diseases; investigation can be conducted into patients' nucleotide sequences hybridized with the probe capable of detecting the disease genes.

The blocker and opener agents for the potassium channel have heretofore been used as therapeutics against diabetes and hypertension. $uK_{ATP}$-1 and its mutants, their derivatives and monoclonal antibodies to them, when processed into pharmaceutical preparations, can be administered to patients to thereby alleviate through neutralization the adverse effects brought about by an excess of such blocker or opener agents administered clinically. When $uK_{ATP}$-1 itself shows functional insufficiency, such pharmaceutical preparations can be administered to thereby make up for such deficient functions of $uK_{ATP}$-1.

The present invention comprises the preparation of drugs for gene therapy being applicable in the essential treatment method. The nucleotide sequences for $uK_{ATP}$-1 or its mutants and their derivatives can be incorporated into plasmid or stem cells, which are then given patients to open up the possibility of finding application as a drug for gene therapy.

Below described are the examples to illustrate the present invention in more detail, while referring to the appended drawings.

BRIEF DESCRIPTION OF THE DRAWINGS

FIG. 1 (SEQ ID NO:1) is an illustration of the amino acid sequences corresponding to the base sequences as shown in FIGS. 2 (SEQ ID NO: 2) and 3 (SEQ ID NO: 3).

FIG. 2 (SEQ ID NO:2) is an illustration of the base sequence of $uK_{ATP}$-1 of a human origin as obtained in Example 5.

FIG. 3 (SEQ ID NO: 3) is an illustration of the amino acid sequence corresponding to FIGS. 5 and 6.

FIG. 4 (SEQ ID NO: 4) is an illustration of the base sequence of $ruK_{ATP}$-1 of a rat origin.

EXAMPLE 1 cDNA Cloning of a Novel Inward Rectifier Potassium Channel ($ruK_{ATP}$-1)

Figure 5A:
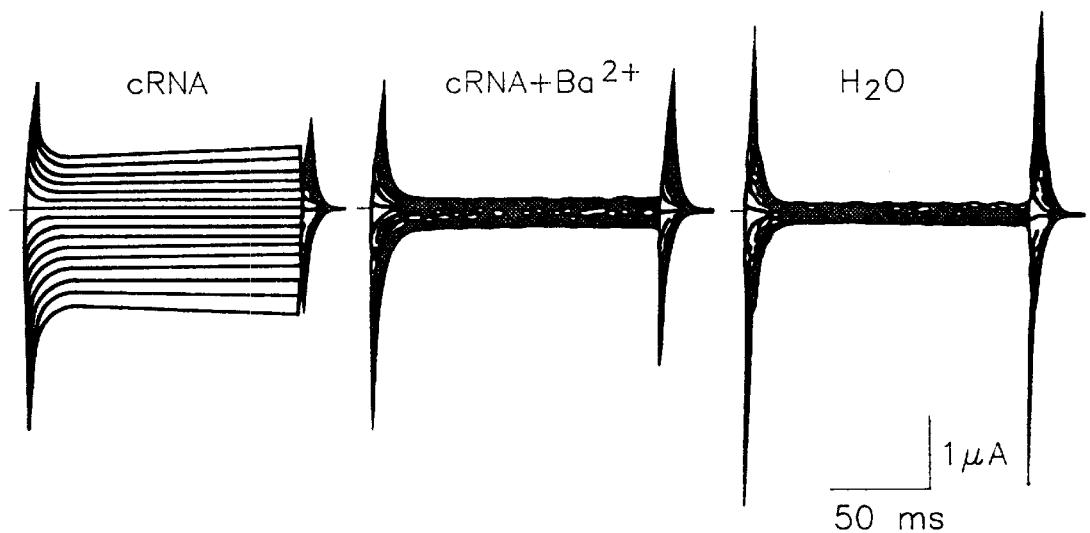
FIG. 5A shows the results of electrophysiological analysis of $ruK_{ATP}$-1 with use of Xenopus oocytes. The oocytes injected with cRNA of $rUK_{ATP}$-1 exhibited inward rectification under conditions of 45 mM [K$^+$] concentrated extracellular fluid, which rectification was however blocked with 300 $\mu$M of Ba$^{2+}$ added to the extracellular fluid. The control, which comprised injection of water, was observed to produce negligible slight inward electric current alone.
Figure 5B:
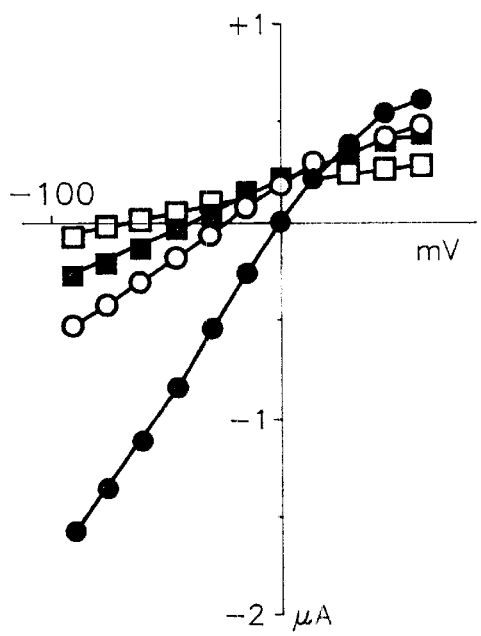
FIG. 5B is a plot of potassium-concentration dependent electric current versus voltage, leading to the confirmation that the $uK_{ATP}$-1 evidently is an inward rectifier potassium channel.
Figure 5C:
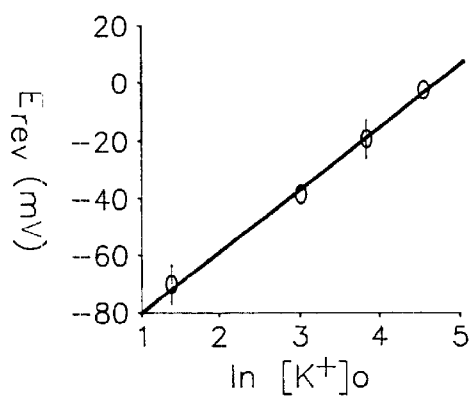
FIG. 5C is a plot of reversible voltage versus a logarithm of extracellular K$^+$ concentration in the oocyte injected with cRNA for $ruK_{ATP}$-1, indicating the dependency of the reversible voltage on the extracellular K$^+$ concentration.
Figure 6A:
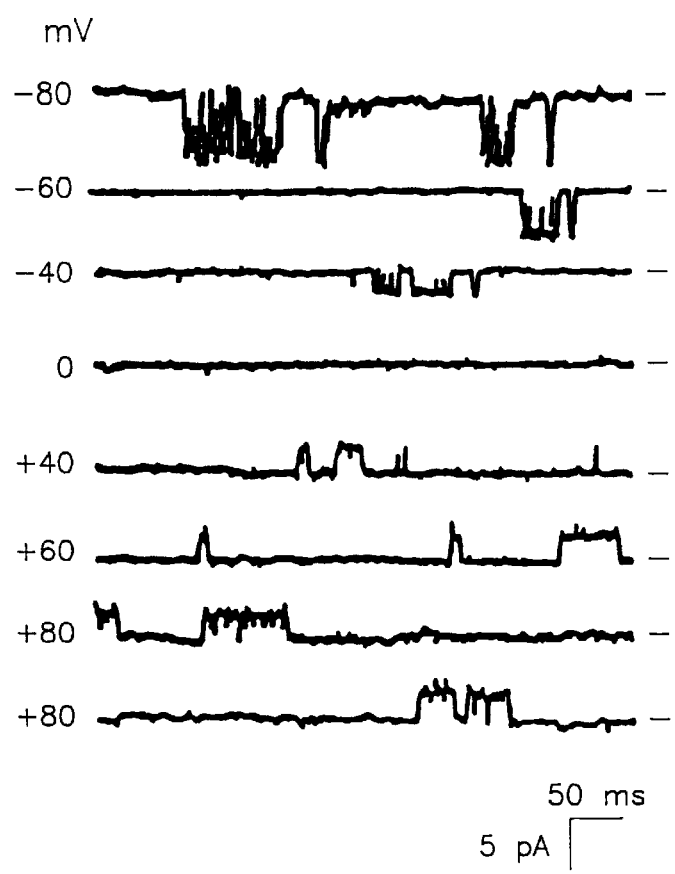
FIG. 6 is a single-channel analysis of HEK 239 transformed cells having $uK_{ATP}$-1 expressed the rein, wherein A represents recordings of single-channel current and B is a current-voltage relationship, demonstrating the presence of a K$^+$ current showing inward rectification.
Figure 6B:
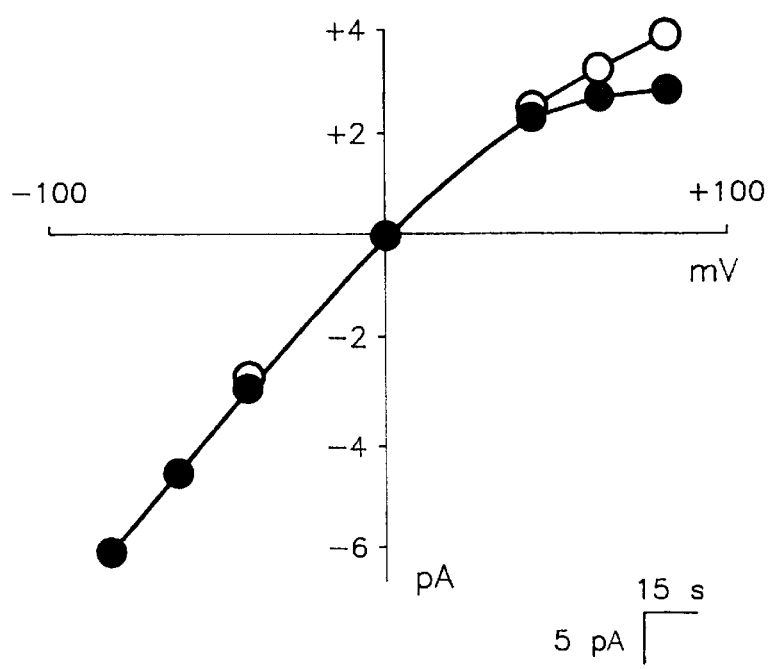

A cDNA fragment of GIRK, rat G protein regulating, inward rectifier potassium channel, was amplified by the polymerase chain reaction (PCR) method. Using a $^{32}$P-labeled rat GIRK cDNA fragment as a probe, search was made into a cDNA library made from rat islets of Langerhans in the vector of λgt22. The isolated $ruK_{ATP}$-1 cDNA was cut into suitable DNA fragments, and after subcloning into M13mp18 or mp19, base sequencing was performed by the chain terminator method (see FIGS. 5 and 6).

EXAMPLE 2

Expression in Xenopus Laevis Oocytes and Electrophysiological Analysis

A 20 ng quantity of cRNA synthesized in vitro from plasmid pGEM11Z containing a full-length $ruK_{ATP}$-1 cDNA with the RNA polymerase after being linearized through treatment with a restriction enzyme Not1 was injected into Xenopus oocytes, followed by electrophysiological analysis 2 or 3 days later. (see FIG. 7). As is illustrated in FIGS. 7A and 7B, there was observed a K$^+$ electric current showing weak inward rectification. The K$^+$ electric current was suppressed by adding Ba$^{2+}$ in the exracellular fluid.

EXAMPLE 3

Single-channel Analysis of HEK 239 Cells Having $ruK_{ATP}$-1 Expressed

HEK 239 cells were cultured in minimum essential Eagle's medium supplemented with 10% of horse serum. The expression plasmid (pCMV6b) carrying a full-length $ruK_{ATP}$-1 coding cDNA was transfected into HEK 239 cells with use of Lipofectamine to prepare transformed HEK 293 cells. The transformed cells produced in this. manner were subjected to single channel analysis, with the results being shown in FIGS. 8A and 8B.

As is evident in FIGS. 8A and 8B, the outward electric current flowing through the channel was suppressed by the intracellular Mg$^{2+}$, revealing that $uK_{ATP}$-1 is an inward rectifier K$^+$ channel; $uK_{ATP}$-1 exhibited a single-channel conductance of ca. 70 pS. FIG. 7 illustrates effects of ATP on the $uK_{ATP}$-1 channel activity as observed in the inside-out mode. When 1 $\mu$M of ATP was added inside the cellular membrane, the channel was open but closed completely upon addition 1 mA of ATP. The results indicate that $uK_{ATP}$-1 is an ATP-regulated $K_{ATP}$ channel.

EXAMPLE 4

RNA Blotting Analysis

A 20 $\mu$g portion of RNA extracted individually from various tissues and cell lines as well as 10 $\mu$g of RNA extracted from the pituitary and thyroid glands were denatured with formaldehyde and electrophoresed on 1% agarose gel, followed by transferring onto a Nylon membrane. Using $^{32}$P labeled $ruK_{ATP}$-1 cDNA as a probe, hybridization was carried out, with the expression of $uK_{ATP}$-1 mRNA being observed in almost all tissues.

EXAMPLE 5

Cloning of cDNA and Gene of $uK_{ATP}$-1 of a Human Origin

In order to isolate cDNA encoding $uK_{ATP}$-1 of a human origin, search was effected into a human lung cDNA library using $^{32}$P labeled $ruK_{ATP}$-1 cDNA of a rat origin as a probe. The resultant clone was subjected to sub-cloning into M13mp18, M13mp19 and pGEM3Z, followed by base sequencing by the chain terminator method.

What is claimed is:

1. An isolated deoxyribonucleic acid molecule comprising a base sequence which encodes a mammalian uK$_{ATP}$-1 ATP-sensitive potassium channel protein.

2. The isolated deoxyribonucleic acid molecule of claim 1, wherein the protein exhibits the biological activity of an ATP-sensitive potassium channel, said molecule further comprising a base sequence encoding another protein or polypeptide linked to either the 5' end or 3' end of said molecule.

3. An expression plasmid comprising the deoxyribonucleic acid of claim 1 or 2 operatively linked to a promoter.

4. A transfected cell containing the plasmid of claim 3.

5. An isolated DNA probe comprising a fragment of a nucleic acid sequence encoding a mammalian uK$_{ATP}$-1 ATP-sensitive potassium channel protein, said fragment having sufficient length to hybridize specifically with said nucleic acid sequence.

* * * * *

UNITED STATES PATENT AND TRADEMARK OFFICE
CERTIFICATE OF CORRECTION

PATENT NO.   : 6,492,167 B2
DATED        : December 10, 2002
INVENTOR(S)  : Seino et al.

It is certified that error appears in the above-identified patent and that said Letters Patent is hereby corrected as shown below:

Column 2,
Lines 20 and 41, change "UK$_{ATP}$-1" to -- uK$_{ATP}$-1 --.

Column 5,
Line 29, change "rUK$_{ATP}$-1" to -- ruK$_{ATP}$-1 --.

Signed and Sealed this

Twenty-fourth Day of June, 2003

JAMES E. ROGAN
*Director of the United States Patent and Trademark Office*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 424 amino acids
      (B) TYPE: amino acid
      (C) STRANDEDNESS: single
      (D) TOPOLOGY: linear (xi) SEQUENCE DESCRIPTION: SEQ ID NO: 1:

```
Met Leu Ala Arg Lys Ser Ile Ile Pro Glu Glu Tyr Val Leu Ala Arg
                 5                  10                  15
Ile Ala Ala Glu Asn Leu Arg Lys Pro Arg Ile Arg Asp Arg Leu Pro
                20                  25                  30
Lys Ala Arg Phe Ile Ala Lys Ser Gly Ala Cys Asn Leu Ala His Lys
                35                  40                  45
Asn Ile Arg Glu Gln Gly Arg Phe Leu Gln Asp Ile Phe Thr Thr Leu
 50                  55                  60
Val Asp Leu Lys Trp Arg His Thr Leu Val Ile Phe Thr Met Ser Phe
 65                  70                  75                  80
Leu Cys Ser Trp Leu Leu Phe Ala Ile Met Trp Trp Leu Val Ala Phe
                 85                  90                  95
Ala His Gly Asp Ile Tyr Ala Tyr Met Glu Lys Ser Gly Met Glu Lys
                100                 105                 110
Ser Gly Leu Glu Ser Thr Val Cys Val Thr Asn Val Arg Ser Phe Thr
                115                 120                 125
Ser Ala Phe Leu Phe Ser Ile Gln Val Gln Val Thr Ile Gly Phe Gly
                130                 135                 140
Gly Arg Met Met Thr Glu Glu Cys Pro Leu Ala Ile Thr Val Leu Ile
145                 150                 155                 160
Leu Gln Asn Ile Val Gly Leu Ile Ile Asn Ala Val Met Leu Gly Cys
                165                 170                 175
Ile Phe Met Lys Thr Ala Gln Ala His Arg Arg Ala Glu Thr Leu Ile
                180                 185                 190
Phe Ser Arg His Ala Val Ile Ala Val Arg Asn Gly Lys Leu Cys Phe
                195                 200                 205
Met Phe Arg Val Gly Asp Leu Arg Lys Ser Met Ile Ser Ala Ser
                210                 215                 220
Val Arg Ile Gln Val Val Lys Lys Thr Thr Thr Pro Glu Gly Glu Val
225                 230                 235                 240
Val Pro Ile His Gln Leu Asp Ile Pro Val Asp Asn Pro Ile Glu Ser
                245                 250                 255
Asn Asn Ile Phe Leu Val Ala Pro Leu Ile Ile Cys His Val Ile Asp
                260                 265                 270
Lys Arg Ser Pro Leu Tyr Asp Ile Ser Ala Thr Asp Leu Ala Asn Gln
                275                 280                 285
Asp Leu Glu Val Ile Val Ile Leu Glu Gly Val Val Glu Thr Thr Gly
                290                 295                 300
Ile Thr Thr Gln Ala Arg Thr Ser Tyr Ile Ala Glu Glu Ile Gln Trp
305                 310                 315                 320
Gly His Arg Phe Val Ser Ile Val Thr Glu Glu Glu Gly Val Tyr Ser
```

```
                    325                 330                 335
Val Asp Tyr Ser Lys Phe Gly Asn Thr Val Lys Val Ala Ala Pro Arg
            340                 345                 350
Cys Ser Ala Arg Glu Leu Asp Glu Lys Pro Ser Ile Leu Ile Gln Thr
        355                 360                 365
Leu Gln Lys Ser Glu Leu Ser His Gln Asn Ser Leu Arg Lys Arg Asn
    370                 375                 380
Ser Met Arg Arg Asn Asn Ser Met Arg Arg Asn Asn Ser Ile Arg Arg
385                 390                 395                 400
Asn Asn Ser Ser Leu Met Val Pro Lys Val Gln Phe Met Thr Pro Glu
            405                 410                 415
Gly Asn Gln Asn Thr Ser Glu Ser
            420
```

(2) INFORMATION FOR SEQ ID NO: 2:

(i) SEQUENCE CHARACTERISTICS:
        (A) LENGTH: 1275 base pairs
        (B) TYPE: nucleic acid
        (C) STRANDEDNESS: single
        (D) TOPOLOGY: linear (xi) SEQUENCE DESCRIPTION: SEQ ID NO: 2:

```
ATGTTGGCCA GAAAGAGTAT CATCCCGGAG GAGTATGTGC TGGCGCGCAT CGCCGCAGAG     60
AACCTGCGCA AGCCGCGCAT CCGAGACCGC CTCCCCAAAG CCCGCTTCAT CGCCAAGAGC    120
GGGGCCTGCA ACCTGGCGCA TAAGAACATC CGTGAGCAAG GACGCTTTCT ACAGGACATC    180
TTCACCACCT TGGTGGACCT GAAATGGCGC ACACGCTGG TCATCTTTAC CATGTCCTTC     240
CTCTGCAGCT GGCTGCTCTT CGCTATCATG TGGTGGCTGG TGGCCTTTGC CCATGGGGAC    300
ATCTATGCTT ACATGGAGAA AAGTGGAATG GAGAAAAGTG GTTTGGAGTC CACTGTGTGT    360
GTGACTAATG TCAGGTCTTT CACTTCTGCT TTTCTCTTCT CCATTGAAGT TCAAGTTACC    420
ATTGGGTTTG GAGGGAGGAT GATGACAGAG GAATGCCCTT TGGCCATCAC GGTTTTGATT    480
CTCCAGAATA TTGTGGGTTT GATCATCAAT GCAGTCATGT TAGGCTGCAT TTTCATGAAA    540
ACAGCTCAGG CTCACAGAAG GGCAGAAACT TTGATTTTCA GCCGCCATGC TGTGATTGCC    600
GTCCGAAATG GCAAGCTGTG CTTCATGTTC CGAGTGGGTG ACCTGAGGAA AAGCATGATC    660
ATTAGTGCCT CTGTGCGCAT CCAGGTGGTC AAGAAAACAA CTACACCTGA AGGGGAGGTG    720
GTTCCTATTC ACCAACTGGA CATTCCTGTT GATAACCCAA TCGAGAGCAA TAACATTTTT    780
CTGGTGGCCC CTTTGATCAT CTGCCACGTG ATTGACAAGC GCAGTCCCCT GTATGACATC    840
TCAGCAACTG ACCTGGCCAA CCAAGACTTG GAGGTCATAG TTATTCTGGA AGGAGTGGTT    900
GAAACTACTG GCATCACCAC ACAAGCACGA ACCTCCTACA TTGCTGAGGA CATCCAATGG    960
GGCCACCGCT TTGTGTCCAT TGTGACTGAG GAAGAAGGAG TGTATTCTGT GGATTACTCC   1020
AAATTTGGCA ACACTGTTAA GTAGCTGCT CCACGGTGCA GTGCCCGAGA GCTGGATGAG    1080
AAACCTTCCA TCCTTATTCA GACCCTCCAA AAGAGTGAAC TGTCTCATCA AAATTCTCTG   1140
AGGAAGCGCA ACTCCATGAG AAGAAACAAT TCCATGAGGA GGAACAATTC TATCCGAAGG   1200
AACAATTCTT CCCTCATGGT ACCAAAGGTG CAATTTATGA CTCCAGAAGG AAATCAAAAC   1260
ACATCGGAAT CATGA                                                    1275
```

(2) INFORMATION FOR SEQ ID NO: 3:

(i) SEQUENCE CHARACTERISTICS:

(A) LENGTH: 424 amino acids
(B) TYPE: amino acid
(C) STRANDEDNESS: single
(D) TOPOLOGY: linear (xi) SEQUENCE DESCRIPTION: SEQ ID NO: 3:

Met Leu Ala Arg Lys Ser Ile Ile Pro Glu Glu Tyr Val Leu Ala Arg
            5                  10                  15

Ile Ala Ala Glu Asn Leu Arg Lys Pro Arg Ile Arg Asp Arg Leu Pro
            20                  25                  30

Lys Ala Arg Phe Ile Ala Lys Ser Gly Ala Cys Asn Leu Ala His Lys
            35                  40                  45

Asn Ile Arg Glu Gln Gly Arg Phe Leu Gln Asp Ile Phe Thr Thr Leu
 50                  55                  60

Val Asp Leu Lys Trp Arg His Thr Leu Val Ile Phe Thr Met Ser Phe
 65                  70                  75                  80

Leu Cys Ser Trp Leu Leu Phe Ala Ile Met Trp Trp Leu Val Ala Phe
                85                  90                  95

Ala His Gly Asp Ile Tyr Ala Tyr Met Glu Lys Gly Ile Thr Glu Lys
                100                 105                 110

Ser Gly Leu Glu Ser Ala Val Cys Val Thr Asn Val Arg Ser Phe Thr
                115                 120                 125

Ser Ala Phe Leu Phe Ser Ile Glu Val Gln Val Thr Ile Gly Phe Gly
 130                 135                 140

Gly Arg Met Met Thr Glu Glu Cys Pro Leu Ala Ile Thr Val Leu Ile
 145                 150                 155                 160

Leu Gln Asn Ile Val Gly Leu Ile Ile Asn Ala Val Met Leu Gly Cys
                165                 170                 175

Ile Phe Met Lys Thr Ala Gln Ala His Arg Arg Ala Glu Thr Leu Ile
                180                 185                 190

Phe Ser Arg His Ala Val Ile Ala Val Arg Asn Gly Lys Leu Cys Phe
                195                 200                 205

Met Phe Arg Val Gly Asp Leu Arg Lys Ser Met Ile Ile Ser Ala Ser
 210                 215                 220

Val Arg Ile Gln Val Val Lys Lys Thr Thr Thr Pro Glu Gly Glu Val
 225                 230                 235                 240

Val Pro Ile His Gln Gln Asp Ile Pro Val Asp Asn Pro Ile Glu Ser
                245                 250                 255

Asn Asn Ile Phe Leu Val Ala Pro Leu Ile Ile Cys His Val Ile Asp
                260                 265                 270

Lys Arg Ser Pro Leu Tyr Asp Ile Ser Ala Thr Asp Leu Val Asn Gln
                275                 280                 285

Asp Leu Glu Val Ile Val Ile Leu Glu Gly Val Val Glu Thr Thr Gly
 290                 295                 300

Ile Thr Thr Gln Ala Arg Thr Ser Tyr Ile Ala Glu Glu Ile Gln Trp
 305                 310                 315                 320

Gly His Arg Phe Val Ser Ile Val Thr Glu Glu Glu Gly Val Tyr Ser
                325                 330                 335

Val Asp Tyr Ser Lys Phe Gly Asn Thr Val Arg Val Ala Ala Pro Arg
                340                 345                 350

Cys Ser Ala Arg Glu Leu Asp Glu Lys Pro Ser Ile Leu Ile Gln Thr
                355                 360                 365

Leu Gln Lys Ser Glu Leu Ser His Gln Asn Ser Leu Arg Lys Arg Asn
 370                 375                 380

```
Ser Met Arg Arg Asn Asn Ser Met Arg Ser Asn Ser Ile Arg Arg
385                 390                 395                 400

Asn Asn Ser Ser Leu Met Val Pro Lys Val Gln Phe Met Thr Pro Glu
                405                 410                 415

Gly Asn Gln Cys Pro Ser Glu Ser
            420

(2) INFORMATION FOR SEQ ID NO: 4:

(i) SEQUENCE CHARACTERISTICS:
        (A) LENGTH: 1275 base pairs
        (B) TYPE: nucleic acid
        (C) STRANDEDNESS: single
        (D) TOPOLOGY: linear (xi) SEQUENCE DESCRIPTION: SEQ ID NO: 4:

ATGCTGGCCA GGAAGAGCAT CATCCCGGAG GAGTATGTGC TGGCCCGCAT CGCGGCGGAG     60

AACCTGCGCA AACCGCGCAT CCGCGACCGC CTCCCCAAAG CCCGCTTCAT CGCCAAGAGC    120

GGAGCCTGCA ACCTGGCTCA CAAGAACATC CGAGAGCAAG GTCGCTTCCT GCAGGACATC    180

TTCACCACCT TGGTAGACCT GAAGTGGCGT CACACGCTGG TCATCTTCAC CATGTCCTTC    240

CTCTGCAGCT GGCTGCTCTT CGCTATCATG TGGTGGCTGG TGGCCTTCGC CCACGGGGAC    300

ATCTATGCTT ACATGGAGAA AGGCATCACG GAGAAGAGTG GCCTGGAGTC TGCCGTCTGT    360

GTGACCAATG TCAGGTCATT CACTTCTGCG TTTCTCTTCT CCATCGAGGT TCAAGTGACC    420

ATTGGGTTTG GAGGGAGAAT GATGACTGAG GAGTGCCCTC TGGCCATCAC GGTTTTGATT    480

CTGCAGAACA TTGTGGGTCT GATCATCAAC GCGGTCATGT TGGGCTGCAT CTTCATGAAG    540

ACGGCCCAGG CCCACAGAAG GGCAGAGACG CTGATTTTCA GCCGCCATGC TGTAATTGCG    600

GTCCGTAATG GCAAGCTGTG CTTCATGTTC CGGGTGGGTG ACCTGAGGAA AAGCATGATC    660

ATTAGCGCCT CGGTGCGCAT CCAGGTGGTC AAGAAAACCA CGACGCCAGA AGGAGAGGTG    720

GTGCCTATTC ACCAGCAGGA CATCCCTGTG GATAATCCCA TCGAGAGCAA TAACATCTTC    780

CTAGTGGCCC CTTTGATCAT CTGCCATGTG ATTGATAAGC GTAGCCCCCT GTACGATATC    840

TCAGCCACTG ACCTTGTCAA CCAAGACCTG GAGGTCATAG TGATTCTCGA GGGCGTGGTG    900

GAAACCACGG GCATCACCAC GCAAGCGCGG ACCTCCTACA TTGCAGAGGA GATCCAGTGG    960

GGACACCGCT TCGTGTCGAT TGTGACTGAG GAGGAGGGAG TGTACTCTGT GGACTATTCT   1020

AAATTTGGTA ATACTGTGAG ACTGGCGGCG CCAAGATGCA GTGCCCGGGA GCTGGACGAG   1080

AAACCTTCCA TCTTGATTCA GACCCTCCAA AAGAGTGAAC TGTCGCACCA GAATTCTCTG   1140

AGGAAGCGCA ACTCTATGAG AAGAAACAAC TCCATGAGGA GGAGCAACTC CATCCGGAGG   1200

AATAACTCTT CCCTCATGGT GCCCAAGGTG CAATTCATGA CTCCAGAAGG AAACCAGTGC   1260

CCATCAGAAT CATGA                                                    1275
```